United States Patent [19]

Woller

[11] Patent Number: 5,320,838

[45] Date of Patent: Jun. 14, 1994

[54] PROTECTANT FOR IRRITATED SKIN CONTAINING POLYETHYLENEGLYCOLS, POLYVINYLETHER SALT ANHYDRIDE AND POLYVINYLPYRROLIDONE

[75] Inventor: William H. Woller, San Antonio, Tex.

[73] Assignee: Pro Cure Products, Ltd., Wilmington, Del.

[21] Appl. No.: 994,279

[22] Filed: Dec. 21, 1992

[51] Int. Cl.$^5$ ................... A61K 31/80; A61K 31/79
[52] U.S. Cl. ................... 424/78.02; 424/78.32; 424/78.33
[58] Field of Search ............ 514/772.5; 424/78.02, 424/78.03, 78.06, 78.32, 78.33, 78.08

[56] References Cited

U.S. PATENT DOCUMENTS

| | | | |
|---|---|---|---|
| 3,608,070 | 9/1991 | Nouvel | 514/772.5 |
| 3,876,771 | 4/1975 | Denner | 424/78.02 |
| 4,478,853 | 10/1984 | Chaussee | 424/358 |
| 4,834,970 | 5/1989 | Login et al. | 424/70 |
| 4,970,220 | 11/1990 | Chaussee | 514/358 |
| 5,043,161 | 8/1991 | Scarpelli et al. | 424/401 |
| 5,110,585 | 5/1992 | Chaudhuri et al. | 424/70 |
| 5,130,121 | 7/1992 | Kopolow et al. | 424/47 |
| 5,139,770 | 8/1992 | Shih et al. | 424/59 |

OTHER PUBLICATIONS

Trade Bulletin on CARBOWAX Polyethylene Glycols and CARBOWAX Methoxy Polyethylene Clycols.
Trade Bulletin on CARBOWAX 3350, of Union Carbide (1991).
Trade Bulletin for GANTREZ.
Dow Corning Trade Bulletin on Silicone Products (1987).
GAF Bulletin on PLASDONE K-90.

Primary Examiner—Thurman K. Page
Assistant Examiner—Peter Kulkosky
Attorney, Agent, or Firm—Zarley, McKee, Thomte, Voorhees, & Sease

[57] ABSTRACT

A smooth, greaseless skin ointment especially prepared for irritated skin, which protects, adheres and simultaneously is easily washable without causing skin damage. The ointment base is a blend of polyethylene glycols. It is combined with a bioadhesive which works synergistically to allow the blended ointment base to adhere to wet and moist areas, while not being so adhesive as to cause damage when removed in washing. Specifically a blend of polyethylene glycol polymers is prepared to provide good skin feel and drag, a polyvinyl ether anhydride salt bioadhesive is added and a polyvinylpyrrolidone is also used as a dispersant, and feces and urine toxicant binder. Optionally minor amounts of dimethicone can be added.

9 Claims, No Drawings

PROTECTANT FOR IRRITATED SKIN CONTAINING POLYETHYLENEGLYCOLS, POLYVINYLETHER SALT ANHYDRIDE AND POLYVINYLPYRROLIDONE

BACKGROUND OF THE INVENTION

This invention relates to a skin protectant, usually for use after skin cleansing. It is a protectant that is especially designed for irritated or compromised skin.

Ointments to be used on irritated skin in order to eliminate the pain and irritating feeling are known. Most are petrolatum based and contain a zinc oxide pigment in order to enhance wound healing.

A significant problem in use of these presently available skin protectants, which are ointment based and contain zinc oxide, is that they in fact do not ideally protect compromised areas. Moreover, the presence of zinc oxide, often compounds the problem of difficulty of removal during wound cleansing. Put another way, because the zinc oxide is somewhat difficult to remove, a nurse applicator is apt to over scrub in cleansing in order to remove zinc oxide. As a result, irritation is exacerbated, skin may be compromised or torn, and the ultimate healing process is delayed.

Problems such as those above described are very common in association with chronic diarrhea, enzymatic drainage, or incontinence. For use with these three problems particularly, a skin protectant needs to one which is greaseless, which provides a good moisture barrier, and one with excellent adhesion to both moist and dry skin.

It is a primary objective invention to provide a skin protectant which is especially designed for use with irritated skin normally associated with chronic diarrhea, enzymatic drainage or incontinence.

It is a further object of the present invention to provide a skin protectant which adheres to both moist and dry skin, and yet which can be easily removed during wound cleansing, without compromising or tearing the skin.

Another object of the present invention is to provide a non-greasy ointment that does not contain zinc oxide.

A further objective of the present invention is to provide an ointment especially usable for compromised or torn tissue which has just the right amount of drag or feel, such that it can be applied to provide a pleasant feeling and for good adherence and yet not being so tacky as to tear skin.

A yet further object of the present invention is to provide a skin protectant which is not petrolatum based, and which is easy to formulate suitable for tubular dispensers.

The method and manner of accomplishing each of the above objectives as well as others will become apparent from the detailed description of the invention which follows.

SUMMARY OF THE INVENTION

A smooth, greaseless skin ointment which can be applied to provide skin protective features on irritated and compromised skin while simultaneously being easy to remove. It comprises a blend of polyethylene glycol polymers designed especially to provide a viscosity suitable for pleasant skin feel without tearing the skin, and to provide such a blend which has adhesiveness such that it will stay on moist skin, not run off, and yet be easy to remove. The composition also contains a polyvinyl ether and polyvinylpyrrolidone in critical proportions to provide the adhesiveness characteristics to both moist and dry skin and yet also be easy to remove during cleansing.

DETAILED DESCRIPTION OF THE INVENTION

In its broadest sense, the invention comprises three major ingredients. The first major ingredient is a blend of polyethylene glycols with one of those comprising from 50% to 80% by weight of the composition, and the other from 15% to 35% by weight of the composition. The second major ingredient is a polyvinyl ether bioadhesive comprising from about 1% to about 30% by weight of the composition. The third major ingredient is polyvinylpyrrolidone at a level of from about 0.5% to about 30% by weight of composition. Optionally the composition may also contain a silicone, (dimethicone) at a weight ratio of from 0.1% to 5%. Each of the ingredients will be described in the order here presented.

Polyethylene glycols are known and are commercially available under the trademark CARBOWAX ® from Union Carbide. They are generally a family of linear polymers formed by the addition reaction of ethylene oxide. The generalized formula for polyethylene is:

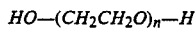

$$HO-(CH_2CH_2O)_n-H$$

wherein "n" is the average number of repeating oxyethylene groups.

The first polyethylene polymer of the blend of this invention is one wherein "n" represents 8.7. It has an average molecular weight of 400. It comprises from about 50% by weight to about 80% by weight of the present invention composition.

The second polyethylene glycol polymer is polyethylene glycol 3350. It has an average molecular weight of 3350. It comprises from 15% to 35% by weight of the composition. When these two polymeric glycols are blended together it provides a homogenous texture and feel. It also provides the correct drag or resistance across skin to be perceived as pleasant, and at the same time, gives a base to the composition which does not simply "run off". These polymers all available commercially from Union Carbide. Detailed literature describing the polyethylene glycols, known as CARBOWAX ® is available upon request from Union Carbide. The presently best known composition of the present invention is one which comprises 69% of the polyethylene glycol average molecular weight 400 and 25% of the polyethylene glycol average molecular weight 3350. CARBOWAX ® 3350 has an average number of repeating oxyethylene units i.e. "n" of 75.7.

It is this blend of the two polyethylene glycols which forms the ointment base and are collectively referred to as the first major ingredient.

The second major ingredient in the present invention is a bioadhesive which is not irritating and which will provide effective adhesiveness for both moist and dry skin. The adhesive found to effectively coact with the polyethylene based ointment blend is a vinyl ether polymer. Particularly preferred is a mixed sodium calcium salt of polymethylvinyl ether/maleic anhydride. It has the basic repeating structure:

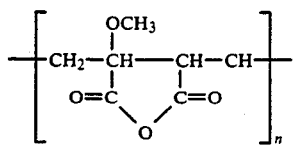

It is readily dispersible to form colloidal dispersions in a wide range of media. It has high tack properties, especially suitable for adhesive applications. It has in the past been suggested for use as denture adhesive and for ostomy products. It also has excellent cold water solubility for easy removal upon washing. It is commercially available under the name GANTREZ MS-955 from GAF Corp. The amount used for the present invention is from 1% to about 30% by weight, preferably from about 2% to about 5% and most preferably 3%.

The third major ingredient of the composition of this invention is polyvinylpyrrolidone, commonly referred to as PVP. It too is available from GAF Corp., under the commercial product name PLASDONE K-90. It is a highly pure, flake-like powder of the chemical structure:

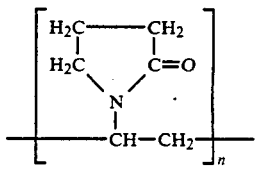

It has a weight average molecular weight of 1,200,000 and is used to provide a colloidal protectant, and as well functions in the present composition as a detoxicant for toxins of feces and urine. That is to say it binds them so that they will not have access to a wound.

It is the combination and coaction of polyvinyl ether and the polyvinylpyrrolidone in connection with the polyethylene blend ointment base which provides the excellent skin protectant nature of the present invention when blended in the amounts described. And it results in a type of skin protectant heretofore never achievable for nonpetrolatum based protectant for irritated skin.

Optimally small amounts of a silicone can be added to enhance the elegance of the composition. Non-volatile polyalkylsiloxanes include, for example, polydimethylsiloxanes (Dimethicone) with viscosities ranging from about 5-600,000 centistokes (cs) at 25° C. These siloxanes are available, for example, from the General Electric Company as the VISCASIL series and from Dow Corning as the Dow Corning 200 products. Preferably, the viscosity of these siloxanes selected have a viscosity of about 100 to about 100,000 cs, and most preferably, a viscosity of up to about 15,000 cs.

Suitable non-volatile polyalkylaryl siloxanes include, for example, polymethylphenyl siloxanes having viscosities of about 15 to 65 cs at 25° C. These siloxanes are available, for example, from the General Electric as SF 1075 methylphenyl fluid or from Dow Corning as 556 Cosmetic Grade Fluid. Additionally, poly(dimethylsiloxane) (diphenylsiloxane) copolymers having a viscosity in the range of about 10 to 100,000 cs at 25° C. are useful.

The following examples are offered to further illustrate but not limit the process and product of the present invention.

EXAMPLES

| Component | (Formulation) % W/W | Amount |
|---|---|---|
| Polyethylene Glycol 400, NF | 69.0 | 483 Kg |
| Polyethylene Glycol 3350, NF | 25.0 | 175 Kg |
| Polyvinyl Ether, Mixed Na/Ca, salt | 3.0 | 21 Kg |
| Polyvinylpyrrolidone | 2.0 | 14 Kg |
| Dimethicone | 1.0 | 7 Kg |

The above composition was examined, found to be nonirritating, non greasy, easily wash removed without skin tearing, particular for incontinent patients and easily packaged in tube dispensers.

In particular, ten patients were treated in an open clinical study with the foam and spray cleanser formulation of copending commonly assigned application Woller, Ser. No. 07/993,412, filed Dec. 21, 1992. Thereafter they used the skin protectant formulation here described.

The clinical profiles of the ten patients used in this test varied from incontinent of bowel with Foley catheter to experiencing erythema, edema, maceration, bleeding and/or ulceration in the perineal, and not responding to treatments within continent wash and moisture barrier ointment/zinc oxide ointment mixture, and patients with skin irritations in the perineal area. Overall the open clinical involved two investigators at separate hospitals treating a total of ten patients. Eight patients suffering from erythema, edema, maceration, bleeding and/or ulceration in the perineal area, were treated as above described. Overall the investigators obtained the following results.

Seven patients with erythema, edema, maceration, bleeding and/or ulceration who had not responded to previous treatment protocols lasting two days to one month, healed within three to twelve days. One patient with erythema, edema and maceration who had not responded to a previous treatment protocol lasting five days, healed within five days and maintained positive skin integrity for nine days. Two "at risk" patients maintained positive skin integrity for ten to eleven days.

The investigators concluded that the formulation foam cleanser and skin protectant appear to be an effective system to assist the nurse practitioner in managing the skin of the incontinent patient. All showed significant improvement, patients described pain relief in about twenty-four hours, redness and irritation improved, as did skin condition.

It therefore can be seen that the invention accomplished at least all of its stated objectives.

What is claimed is:

1. A smooth greaseless skin ointment especially prepared for irritated skin which will protect and adhere while simultaneously being easily washable without causing skin damage, consisting essentially of:
   (a) from about 50% by weight to about 80% by weight of polyethylene glycol polymer of average molecular weight of about 400;
   (b) from about 15% by weight to about 35% by weight of linear polymer of polyethylene glycol having an average molecular weight of about 3350;
   (c) from about 1% to about 30% by weight of a polyvinyl ether salt anhydride bioadhesive; and (d) from about 0.5% by weight to about 30% by weight of polyvinylpyrrolidone.

2. The composition of claim 1 wherein the amount of linear polyethylene glycol of average molecular weight 400 is about 69% and the amount of linear polyethylene glycol polymer 3350 is about 25%.

3. A composition of claim 1 wherein the polyvinyl ether sodium calcium mixed salt anhydride has the formula:

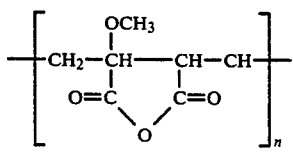

wherein "n" is the number of repeating units.

4. A composition of claim 3 wherein the amount of polyvinyl ether is from 2% to 5% by weight of the composition.

5. A composition of claim 4 wherein the amount of polyvinyl ether is about 3% by weight of the composition.

6. A composition of claim 1 wherein the amount of polyvinylpyrrolidone is from about 1% to about 10% by weight of the composition.

7. The composition of claim 6 wherein the amount of polyvinylpyrrolidone is about 2% by weight of the composition.

8. The composition of claim 1 which contains from about 0.1% to 5% by weight of dimethicone.

9. The composition of claim 8 which contains from about 1% to 2% dimethicone.

* * * * *